(12) United States Patent
Saeed

(10) Patent No.: US 8,821,567 B2
(45) Date of Patent: Sep. 2, 2014

(54) APPARATUS AND METHOD FOR IMPLANTATION OF A BIFURCATED ENDOVASCULAR PROSTHESIS

(76) Inventor: Mohsin Saeed, La Jolla, CA (US)

( * ) Notice: Subject to any disclaimer, the term of this patent is extended or adjusted under 35 U.S.C. 154(b) by 719 days.

(21) Appl. No.: 11/888,031

(22) Filed: Jul. 30, 2007

(65) Prior Publication Data

US 2008/0208309 A1    Aug. 28, 2008

Related U.S. Application Data

(60) Provisional application No. 60/903,253, filed on Feb. 22, 2007.

(51) Int. Cl.
*A61F 2/06* (2013.01)

(52) U.S. Cl.
USPC ....... 623/1.35; 623/1.11; 623/1.12; 623/1.23; 606/108

(58) Field of Classification Search
USPC .................... 623/1.13, 1.23, 1.35, 1.11, 1.12; 606/108, 113, 198
See application file for complete search history.

(56) References Cited

U.S. PATENT DOCUMENTS

| | | | |
|---|---|---|---|
| 5,676,697 A | 10/1997 | McDonald | |
| 6,099,558 A * | 8/2000 | White et al. | 623/1.16 |
| 6,264,662 B1 | 7/2001 | Lauterjung | |
| 6,299,634 B1 | 10/2001 | Bergeron | |
| 6,517,550 B1 * | 2/2003 | Konya et al. | 606/113 |
| 6,676,694 B1 | 1/2004 | Weiss | |
| 6,808,534 B1 | 10/2004 | Escano | |
| 6,916,355 B2 | 7/2005 | Kanjii | |
| 6,942,691 B1 | 9/2005 | Chuter | |
| 6,953,475 B2 | 10/2005 | Shaolian et al. | |
| 7,011,679 B2 | 3/2006 | Lauterjung | |
| 7,014,653 B2 | 3/2006 | Ouriel et al. | |
| 7,018,400 B2 | 3/2006 | Lashinski et al. | |
| 7,122,048 B2 | 10/2006 | DiMatteo et al. | |
| 2005/0182476 A1 * | 8/2005 | Hartley et al. | 623/1.11 |
| 2005/0228476 A1 * | 10/2005 | DiMatteo et al. | 623/1.11 |

* cited by examiner

Primary Examiner — Victor Nguyen
Assistant Examiner — Kevin Everage
(74) Attorney, Agent, or Firm — Donn K. Harms

(57) ABSTRACT

A bifurcated stent graft for animal or human implantation and method of delivery thereof. The device stent graft employs a first component having an axial passage communicating with the axial cavities of a second leg and longer first leg. A separate leg extension is engageable to the second leg. A first catheter engages the first component for translation to the implantation site and a second catheter engaged with the first is provided with a prepositioned guide wire inside the second leg which may be employed to easily position a guide wire for engagement of the second leg with the leg extension.

11 Claims, 8 Drawing Sheets

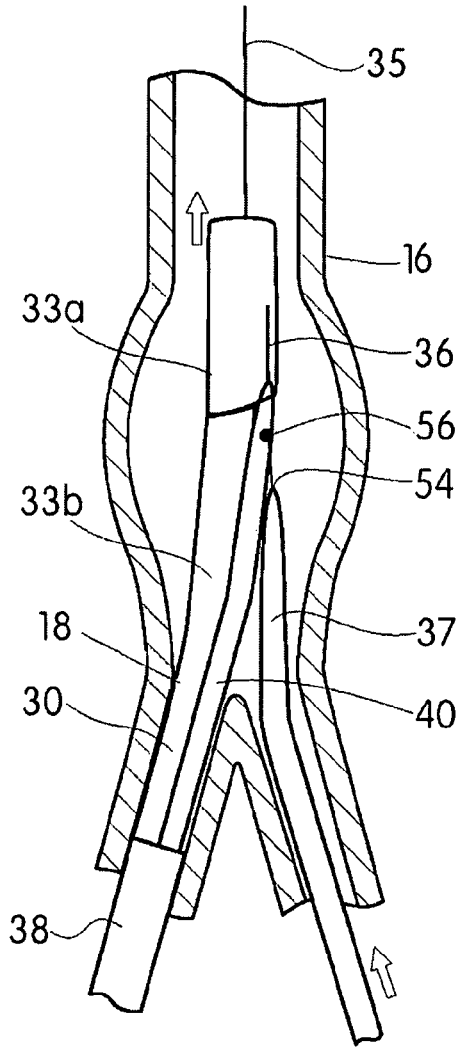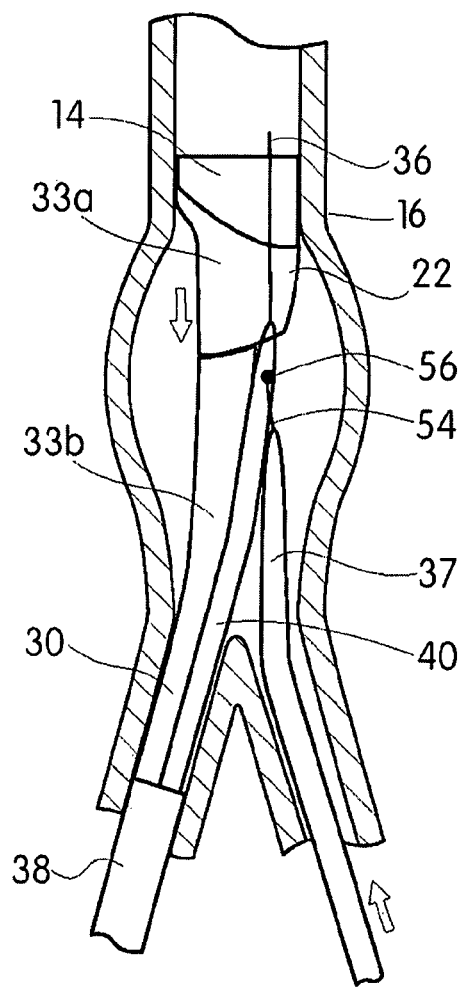
Fig. 5
Fig. 6

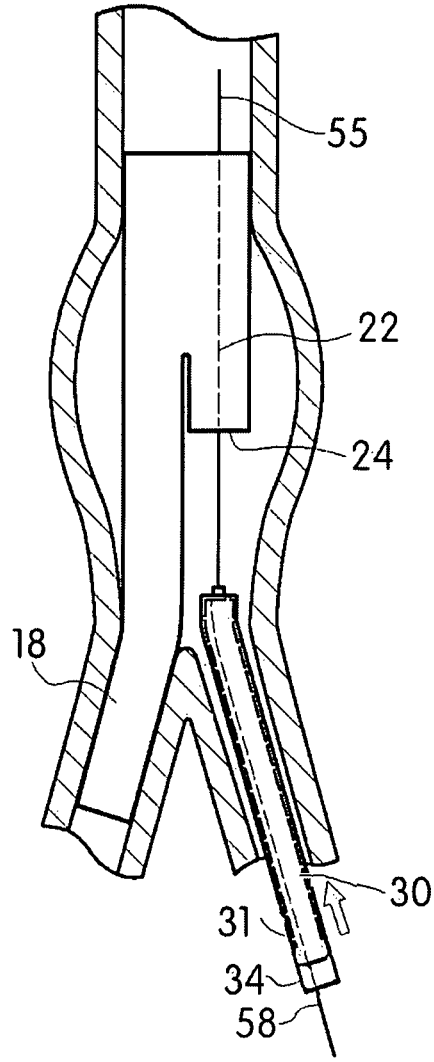
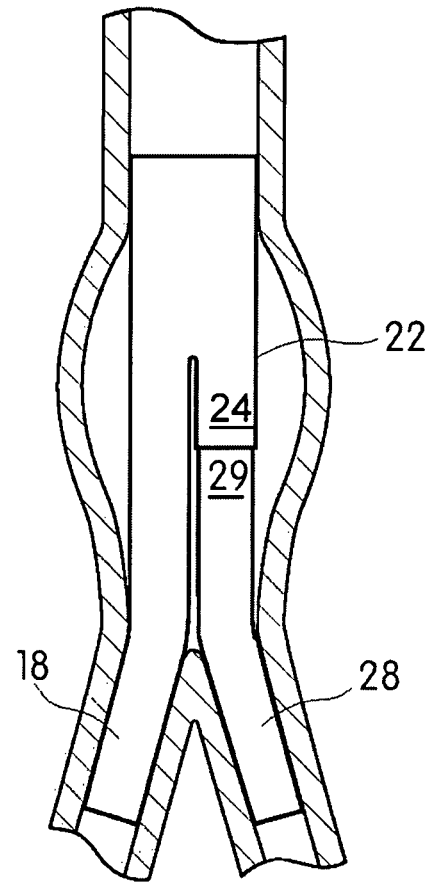
Fig. 9
Fig. 10

APPARATUS AND METHOD FOR IMPLANTATION OF A BIFURCATED ENDOVASCULAR PROSTHESIS

This application claims priority from U.S. Provisional Patent Application Ser. No. 60/903,253 filed Feb. 22, 2007.

FIELD OF THE INVENTION

The disclosed device relates to an endovascular prosthesis and implantation method therefor. More particularly it relates to a device and method for implantation of a bifurcated endoprosthesis for repair of infrarenal abdominal aortic aneurysms commonly known to those skilled in the art as AAA's.

BACKGROUND OF THE INVENTION

An aneurysm is a type of disease that affects the arteries and is manifested by a localized widening or enlargement of an artery compared to its normal size. Because of the potential of rupture of the artery in question, any aneurysm is a serious health problem and risk to a patient. When a blood vessel with an aneurysm ruptures, life-threatening bleeding generally is the result. Even prior to such an occurrence, aneurysms can also cause pain from pressure on nearby organs or nerves and on occasion, debris within the aneurysm can dislodge and thereafter be communicated through the circulatory system of the patient to the legs or vital organs. The result is generally a blocking of the blood flow to these tissues and resulting harm to organs and tissues remote to the aneurysm itself.

A common location for aneurysms is in the abdominal aorta, which is one of the largest blood vessels in the body and located in the abdominal region of the body. A rupture of such a large blood vessel has dire and life threatening consequences to the individual suffering such a crisis. Such abdominal aortic aneurysms (AAA's) most often involve the infrarenal aorta which is the portion of the blood vessel that lies below the takeoff of the arteries to the kidneys (renal arteries). About half of AAA's also involve the iliac arteries in the pelvis. The major risk associated with AAA's is that they have a high propensity to rupture and currently such ruptures are the 13th leading cause of death in the United States. Therefore, early detection and timely repair are paramount to the patient.

Current medical practice which is least invasive to the patient employs endovascular repair or stent grafting, in a procedure which is performed through small incisions in each groin. While carrying many of the same risks as invasive surgical repair, patients usually spend fewer days in the hospital and recover more quickly with less pain with the implantation of an endovascular prosthesis.

In a procedure to implant the prosthesis, a bifurcated stent graft is positioned within the aneurysm to provide a new conduit for blood flow through the damaged portion of the blood vessel. This effectively seals off the diseased and bulging portion of the aorta from the blood flow and eliminates the potential for rupture.

A common endoprosthesis for repair of an AAA is a two-piece bifurcated endovascular graft which is positioned to line the aorta within the aneurysm and has a first portion adapted to engage within the aorta, which communicates with two graft conduits, and which extends from below the renal arteries into both iliac arteries. Material such as ePTFE (expanded polytetrafluoroethylene) forming this fluid conduit for blood flow is commonly inert when implanted. A structural metallic component known generally as a stent is engaged in a skeletal arrangement with the material to maintain the formed conduits for blood flow in an expanded condition once implanted.

Delivery and implantation of the device to the site of the aneurysm in the abdominal aorta is generally done by assembly of two component sections which include the trunk with a cuff adapted to engage the contralateral leg. The trunk portion has a large diameter adapted to engage within the large internal diameter of the aorta and is implanted to a position just below the renal arteries. Extending from the trunk and having an internal conduit in communication with the internal passage of the trunk portion is the ipsilateral leg which is positioned in communication within one of the iliac arteries when deployed. The trunk and first leg are conventionally formed and deployed as a unitary structure. The cuff also extends from the trunk portion and, as noted, is adapted for engagement to the second leg which is positioned once engaged within a second of the iliac arteries. The engagement of the contralateral leg with the cuff and positioning of its distal end within the other of the iliac arteries completes the stent graft.

This two-piece construction yields is required because of the nature of the engagement of the two legs from the trunk into two different iliac arteries. However, assembly of these two components inside the body of the patient during surgery can be a vexing task to even the most experienced and knowledgeable surgeon. This is because the visual display depicting the components during assembly is a two-dimensional video visualization of a three-dimensional communication between the components of the implant and the two iliac arteries in their junction to the aorta. These arteries generally engage with the aorta at angles radial to the axis of the aorta which must be accommodated during the engagement of the contralateral leg portion with the short extending cuff from the trunk portion.

Currently, the trunk portion and first leg portion are advanced using a catheter and guide wire through an incision in one of the femoral arteries. Once inserted into a femoral artery, the trunk and extending first leg and cuff are advanced over the guide wire to the proper position at the juncture of the aorta and renal arteries. During this translation into the aneurysm, the trunk, cuff, and ipsilateral leg are held in a compressed state at the distal end of the catheter by a restraining mechanism which can at a chosen time be released by controls positioned outside the patient's body to allow the stent graft to enlarge to its expanded state, thereby engaging within the vessel at the appropriate point. Once proper positioning is determined by the surgeon using radiopaque markers and fluoroscopic visualization of the distal end of the first catheter, a control mechanism communicating with the restraining mechanism is activated. This allows for enlargement of the trunk and first leg in their respective positions in the aorta and iliac artery.

It is at this point in the procedure that the surgery can become uncertain as to duration and an ongoing source of frustration to the surgeon. Attachment of the second or contralateral leg to the distal end of the cuff portion extending from the trunk is achieved by translating a guide wire from the second leg artery which must be visually guided into the aperture at the distal end of the cuff extending from the trunk. Once so positioned, the contralateral leg may be translated over the guide wire and into proper position relative to the cuff and enlarged to engage the contralateral leg to the cuff.

While this may sound like a simple procedure in principle, in practice it is both frustrating and can be extremely time consuming. The extra time in the operating room and uncertainty as to operation duration impacts the surgery schedules for subsequent surgeries. Additionally, during this engagement process of the contralateral leg to the cuff, the patient remains under anesthesia, exposed to continual x-ray radiation, and subjected to continued manipulation of the guide wire inside the vessel adjacent to the cuff. Since there is usually extensive clot and atherosclerotic plaque within the aneurysm, such manipulation entails the additional risk of dislodging debris within the lumen of the aneurysm, thereby also raising the risk of such debris traveling to branch arteries of the aorta.

The primary problem in this engagement step arises from the wide variance of intersecting angles of the radially extending iliac arteries from the aorta. The resulting angles of the graft legs may be highly divergent from the axis of the trunk. However, in the two-dimensional visualization provided by the fluoroscope, the surgeon is visually hindered in the attempt to thread the guide wire into the aperture at the distal end of the cuff. An additional factor complicating wire passage into the cuff is that the cuff is usually near the center of the large cavity formed by the aneurysm which in many cases can exceed 10 cm in diameter. The engagement of a small diameter cuff positioned in the midst of such a comparatively large space with the aid of only two-dimensional imaging, while concurrently contending with the highly variable angles of approach from the iliac arteries, renders the procedure very unpredictable.

Further, in many cases the angles leading to the iliac arteries from the aorta are such that the surgeon will choose to cross over the first leg and contralateral leg in an overlapping arrangement to maintain a continuous curve for blood flow and to avoid kinks. When graft legs are crossed, attempts at passage of a wire from the second iliac artery into the cuff may additionally be complicated by interference from the first leg which, when positioned in the cross-leg deployment format, will lie across the opening from the second iliac artery into the aorta. Even highly trained surgeons with years of experience can become bogged down trying to thread the guide wire into the aperture of the cuff using the two dimensional visualization and overlapping of images available on the fluoroscopic screen. Absent a lucky positioning of the guide wire, such an exercise can consume an inordinate amount of time.

As such, there exists an unmet need for a bifurcated endoprosthesis which can be more easily assembled from components to repair aortic aneurysms. Such a device should allow for conventional deployment of the trunk portion and first extending leg and cuff in a relatively conventional fashion to facilitate easy adoption of the device and procedure. However, such a device and method should provide a means to eliminate the frustration and time-consuming step requiring the surgeon to fish with the distal end of a second guide wire for the aperture of the cuff extending from the trunk portion. In this fashion implantation surgeries for such devices may be expedited and performed with a reasonably accurate estimate of duration, and patients undergoing such surgeries will benefit from shortened procedures and be spared exposure to prolonged radiation.

In this respect, before explaining at least one embodiment of the invention in detail, it is to be understood that the invention is not limited in its application to the details of construction and to the arrangement of the components set forth in the following description or illustrated in the drawings nor the steps outlined in the specification. The invention is capable of other embodiments and of being practiced and carried out in various ways as those skilled in the art will readily ascertain from reading this application. Also, it is to be understood that the phraseology and terminology employed herein are for the purpose of description and should not be regarded as limiting.

As such, those skilled in the art will appreciate that the conception upon which this disclosure is based may readily be utilized as a basis for designing other methods and systems for carrying out the several purposes of the present invention of a device and method for implanting a bifurcated prosthesis in an aortic aneurysm. It is important, therefore, that the claims be regarded as including such equivalent construction insofar as they do not depart from the spirit and scope of the present invention.

OBJECTS OF THE INVENTION

An object of this invention is the provision of a bifurcated prosthesis for repair of aortic aneurysms.

An additional object of this invention is the provision of such a prosthesis which may be assembled from multiple components with ease and in a much reduced duration from a conventionally available device.

Yet another object of this invention is to provide a plurality of means to restrain the implantable prosthesis in a compressed state such that controlled release of the restraining mechanism employed is achievable. The restraint system allows for incorporation of a novel component adapted for capture of an additional guide wire into the overall apparatus in a manner optimizing function of the device.

Yet another object of this invention is the provision of a method of implantation of such a device which pre-positions the guide wire employed for engagement of a second leg to the trunk portion of the device, thereby eliminating the time-consuming task of fishing for the cuff aperture.

Another object of this invention is to provide a method of capturing a secondary guide wire during assembly of a bifurcated stent graft procedure and guiding it into a targeted aperture using a snare or other capture means which may be engaged to a catheter which will slide on the prepositioned guide wire.

Yet another object of this invention is to provide a device and method of secondary guide wire capture and guide to a target aperture by provision of a catheter and snare combination and pre-positioned second, or escort, catheter.

These together with other objects and advantages which will become subsequently apparent reside in the details of the construction and operation as more fully hereinafter described and claimed, reference being had to the accompanying drawings forming a part thereof, wherein like numerals refer to like parts throughout.

SUMMARY OF THE INVENTION

The device and method herein feature a modular bifurcated vascular prosthesis which is assembled in the artery of a patient from a plurality of components adapted for mutual engagement and placement within a diseased aorta to provide a new conduit for blood flow therethrough.

As currently practiced, attempts to engage the contralateral cuff portion of the graft with a guide wire commence after the graft is deployed. As previously mentioned, this is encumbered by several factors, notably the small size of the target within a large aneurysm cavity, variably complex angles of approach imposed by iliac artery orientation relative to the axis of the aorta, and possible interference from the deployed long leg of the graft when a crossed-leg deployment is chosen.

The device and method disclosed herein obviates these difficulties through employment of several novel strategies and structures. Firstly, the time-consuming and unpredictable requirement of current art to maneuver a direct wire passage from the second iliac artery into the cuff after deployment of the device is eliminated. Instead, a maneuver is substituted which provides for easy capture of a guide wire from a catheter introduced from a second iliac artery by provision of means for capture of its distal end in a positive mechanical engagement.

Because of the manipulation of the device and captured guide wire subsequent to capture, it is especially important that the capture be secure until the surgeon decides to release that capture. This capture device in a current preferred mode employs a snare. The snaring function is enabled by a novel device which is a key component of the overall apparatus. The device, also referred to as the "escort catheter" in the text, is a narrow diameter, semi-rigid catheter having a central coaxial lumen allowing for passage of a second guide wire therethrough over which the catheter can be translated, and which second guide wire can be pre-positioned inside the cuff portion extending from the main trunk of the stent graft.

Also incorporated into the escort catheter is an eccentric lumen the proximal end of which lumen is accessed through a locking, rotatable valve attached externally near the back end of the escort catheter. The distal end of the eccentric lumen communicates with an aperture in the wall of the escort catheter some distance from the distal tip of the escort catheter. A snare wire passes through the locking valve, runs within the eccentric lumen, and has its tip tethered to the catheter wall at the aperture. Forward translation of this wire extrudes a desired length of wire from the aperture, the extruded length assuming the shape of a snare loop, projecting orthogonally to the axis of the catheter. Loop formation and its orthogonal projection are aided by incorporation of pre-shaped memory into the wire.

The snare loop can be closed by retraction of the wire, and held securely in the closed position by locking the rotating valve around the wire. The escort catheter is depicted in FIG. 2, and FIG. 2a illustrates the incorporation of this catheter into the shaft of the main delivery catheter, the function of this integrated unit being detailed elsewhere in the text. Extending from this escort catheter is the second guide wire which is pre-positioned inside the cuff of the graft during assembly. This second guide wire thereby provides a pre-positioned guide for translation of a captured third guide wire directly into the cuff portion of the device.

Additional utility and benefit to the patient is provided by the fact that this capturing maneuver is transferred to a location within the vascular system far more favorable than the center of a large aneurysm cavity. Specifically, capture of the third wire from a second catheter is executed at the confluence of the two iliac arteries as they converge at the bottom of the aneurysm. The second catheter with the third guide wire introduced from the second iliac artery is predictably engaged by the snare loop of desired dimension and shape which projects across the opening of the iliac artery. This arrangement exploits the inevitable convergence of the second catheter and its guide wire and the snare-bearing device engaged with the delivery catheter from the first iliac artery.

Further utility in the disclosed device is provided through the incorporation of the positioning or escort catheter in a translatable communication through the graft-bearing delivery catheter. Such a collinear engagement provides the surgeon freedom of orientation of the snare loop at the opening of the second iliac artery by translation and rotation of the catheter assembly to optimally position the snare for capture of the second guide wire.

Still further, after capture of the third guide wire extending from the second catheter, the entire engaged apparatus can be translated and rotated at will, thereby enabling the surgeon to provide precise graft positioning as well as rotational orientation for crossing the legs of the device to whatever degree is dictated by patient anatomy. Such maneuvers can be executed without risk of loss of the captured third guide wire because of the security conferred by design of the snare and an engagement bead positioned at the distal end of the third guide wire extending from the secondary catheter. This mechanical engagement insures that the capture will remain intact until the surgeon initiates a manual release.

In this particularly preferred mode of the disclosed device and method, a bead is engaged upon the extended third guide wire of the secondary catheter. To allow easy withdrawal of the third guide wire through the secondary catheter, the proximal profile of the bead needs to be tapered so as to align with the lumen easily. This attribute would, however, be in conflict with the requirement that the bead be securely captured in the snare loop, which would be aided by the bead having an abrupt proximal profile.

Therefore, the third guide wire from the secondary catheter in one preferred embodiment employs an abruptly fashioned bead which may not be removable through the lumen of the secondary catheter from which it translates. Using this mode of the device would therefore require a wire exchange be executed by the surgeon using conventional wide lumen sheaths to position a heavy duty angiographic wire inside the cuff over which the contralateral leg may be translated into the cuff.

Of course those skilled in the art will no doubt realize the device may be employed to take advantage of the prepositioned escort catheter guide wire in the cuff of the contralateral leg in combination with the operation of a snare or other means of engagement to secure and guide some type of guide wire from the secondary catheter to be employed to guide the contralateral leg into engagement with the cuff. Further, the method of positioning a capture device adjacent to the distal end of the main delivery catheter and prepositioning a guide wire in the cuff of the contralateral leg may be employed with currently manufactured devices. The employment of this method with all such devices is anticipated as included herein. Still further, while a two-step expansion system is described herein for the trunk and leg portions of the device, it is anticipated that a one-step expansion could be employed in a less preferred method and mode of the device which would require extraction of the second catheter from a position sandwiched between the engaged first leg and the iliac artery, and such is anticipated.

The device herein disclosed, as noted, has a first component which includes a trunk portion with an enlarged diameter adapted to engage within the walls of the aorta. In addition to the trunk portion, the first component has two smaller conduits extending from a lower end of the trunk opposite the open aperture of the trunk portion. An ipsilateral or first leg has a diameter and a length adapted to allow it to extend into an engaged position communicating between the trunk and one of the iliac arteries when the first component portion is deployed to its enlarged position. The other shorter conduit is a cuff portion which also extends from the lower end of the trunk portion. The shorter cuff portion has an aperture at a distal end. The distal end of the cuff is adapted for engagement to an engagement end of the second or contralateral leg which is the second component of the assembled device.

The trunk, first leg, and cuff forming the first component are adapted to be collapsed to a compressed position and held in that state by a removable sheath or other means of releasable restraint of the first component when engaged at the distal end of a first delivery catheter. A release mechanism is engaged within or along the first delivery catheter to allow a sequential release of the restraining mechanism at a desired time in the procedure. In a preferred mode of the device herein disclosed, the releasable restraint would provide two separately releasable component portions that would allow for expansion of the trunk and cuff portions of the device in a first step and the remainder of the device subsequent to engagement of a third guide wire into the cuff portion.

A second component of the device is a second leg portion which is engaged to a second delivery catheter in a collapsed state for translatable delivery along the properly positioned secondary guide wire to an engagement with the expanded cuff of the first component. As noted, the engagement end of the contralateral or second leg is adapted to cooperatively engage with the distal end of the expanded cuff to thereby yield a second conduit for blood flow from the trunk portion and into the second of the two iliac arteries once the device is fully assembled and deployed.

A projecting first guide wire is positioned in the body to provide a guide to the first delivery catheter which is advanced thereover to place the graft-bearing portion or distal end of a first delivery catheter in a proper positioning. The trunk and first leg are held by a fabric sheath or other restraining mechanism in a collapsed position. An escort catheter is slidably engaged within the first delivery catheter and has a projecting end portion which extends from an exit aperture in the first delivery catheter. This end portion is substantially exposed but for a tip portion which is held under the restraint.

A second guide wire extending from the distal end of the escort catheter is pre-positioned within the cuff portion extending from the trunk of the first component prior to compression to the collapsed state. Once in the collapsed state, this second guide wire extending from the projecting end portion of the escort catheter thereby remains pre-positioned in the cuff.

As noted, also incorporated into the escort catheter of the device is a snare which is preferably formed of memory material such as nitinol. This snare is extendable from an exit aperture communicating through the sidewall of an uncovered portion of the escort catheter. A snare control wire for cinching the projecting snare is tranlatably engaged axially through the escort catheter to a rotating valve positioned exterior to the body of the patient. The cinch can thus be extended to an enlarged loop, or collapsed, by translation of the control wire. Using memory material, the enlarged loop may be preformed with a memorized shape and projection, such that the loop so projected is orthogonal to the axis of the escort catheter and is of a size best adapted to the task of capturing a third guide wire extending forward from the secondary catheter which is also operatively engaged to this guide wire.

In the method of implantation, the first component formed of the trunk, first leg, and cuff, in the above noted collapsed position on the end of the first delivery catheter, is translated over a pre-positioned first guide wire through a femoral artery to thereby position the trunk within the aorta at the site of the aneurysm. To this end, the first delivery catheter is extended up through one of the iliac arteries to position the trunk portion in the aorta and concurrently place the first leg within that iliac artery.

Prior to activation of the mechanism which releases a first portion of the employed means for restraining the upper half of the first component in the collapsed position, the snare is extended from the uncovered portion of the escort catheter to form a loop by translating the snare wire. The loop as noted, is positioned at the juncture of the second iliac artery and the aorta by extension of the snare and/or translation of the escort catheter. Once positioning of the first component and the snare is properly confirmed using the fluoroscope or other means, the second catheter is translated up the opposite leg artery toward the first component. The third guide wire extending from the distal end of the secondary catheter and has a bead or small terminating component fixed to its distal end to provide a grip for the snare.

During this step, the distal end of the third guide wire extending from the second catheter is translated to a point wherein it traverses through the extended loop of the projecting snare which is positioned around the iliac artery juncture with the aorta. Once traverse of the second guide wire through the loop of the snare is confirmed, the snare control wire is translated to cinch the loop of the snare and capture the distal end of the third guide wire extending from the second catheter. A locking rotatable valve is then set to hold the snare in the closed position.

At this juncture in the method of deployment the disclosed device with the captured third guide wire may be manipulated into proper position relative to the aorta and iliac arteries by the surgeon to provide a precise graft positioning depending on the surgeon's chosen mode of leg and trunk orientation of the device within the patient. As noted, this maneuver can be accomplished without risk of loss of the captured second guide wire since it is secure in the snare and only subject to release by the positive action of the surgeon to do so. Once properly positioned by the surgeon, the first portion of the compressed first component may be fully deployed from the compressed state to the enlarged state thereby seating the trunk in the aorta and the cuff in expanded mode. The first or longer engaged leg remains compressed for subsequent deployment in the chosen one of the two iliac arteries.

Once the first component is so expanded, the novelty and utility of the disclosed device become evident. Since the third guide wire of the secondary catheter is already captured by the snare, and the second guide wire extending from the escort catheter is pre-positioned within the now expanded cuff, it is a short and simple process to translate the escort catheter, along with the snare-engaged guide wire of the secondary catheter, along the second guide wire into the cuff, and subsequently translate the secondary catheter, or subsequent devices, over the third guide wire and into the cuff.

As noted earlier, with the third guide wire extending from the secondary catheter positioned in the cuff, any of a number of conventional wire exchanges may be executed by the surgeon using this third guide wire from the secondary catheter to place a conventional heavy duty guide wire into the cuff, over which the catheter bearing the contralateral leg may be advanced for engagement into the cuff.

As an example, the surgeon may advance a wide lumen sheath over the third guide wire to thereby position its distal end inside the cuff. Thereafter, the third guide wire may be removed through the wide lumen axial cavity of the sheath and a guide wire of the surgeon's choice may be properly positioned through the axial cavity to place its distal end inside the cuff. Using this subsequently placed wire, the surgeon would then advance a secondary delivery catheter, bearing the second leg, thereover to properly position the contralateral or second leg within the distal end of the cuff. The contralateral leg is then deployed by activating a control to release the constraining mechanism holding it in a collapsed state, as is the first leg in the secondary employment of the first component of the assembled device. Once so deployed, the engagement end of the properly positioned contralateral leg enlarges to a fixed engagement with the cuff thereby providing the second sealed conduit between the aorta-engaged trunk and the second iliac artery. This completes assembly of this device.

As those skilled in the art will realize, other means to releasably engage the secondary catheter guide wire to the escort catheter extending exposed from the first delivery catheter might be employed, and all as would occur to those skilled in the art are anticipated. However, because of the confined working environment, the compactness and ease of operation of the snare, the ability to provide memorized shapes to the snare, and the positive releasable mechanical engagement thereon, the current preferred mode of the device employs the snare to capture the secondary catheter for placement of a third guide wire in the contralateral cuff.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Therefore, the foregoing summary and following detailed description are considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

BRIEF DESCRIPTION OF THE DRAWINGS

FIG. 5 depicts translation of the device into the aorta subsequent to capture of the second lead wire.

FIG. 6 shows initial deployment, by release of a first portion of the two stage restraint through a release of the constraining stitch allowing expansion of the trunk portion of the device in the aorta.

FIG. 9 depicts a subsequent guide wire located in the cuff after the surgeon executes a wire exchange with the second lead wire and a subsequent advancement of the restrained second leg, along the chosen guide wire for engagement in the cuff.

FIG. 10 shows the second leg of the device in an expanded engagement with the cuff subsequent to release of restraint mechanism holding the second leg collapsed.

DETAILED DESCRIPTION OF THE INVENTION

Figure 1:
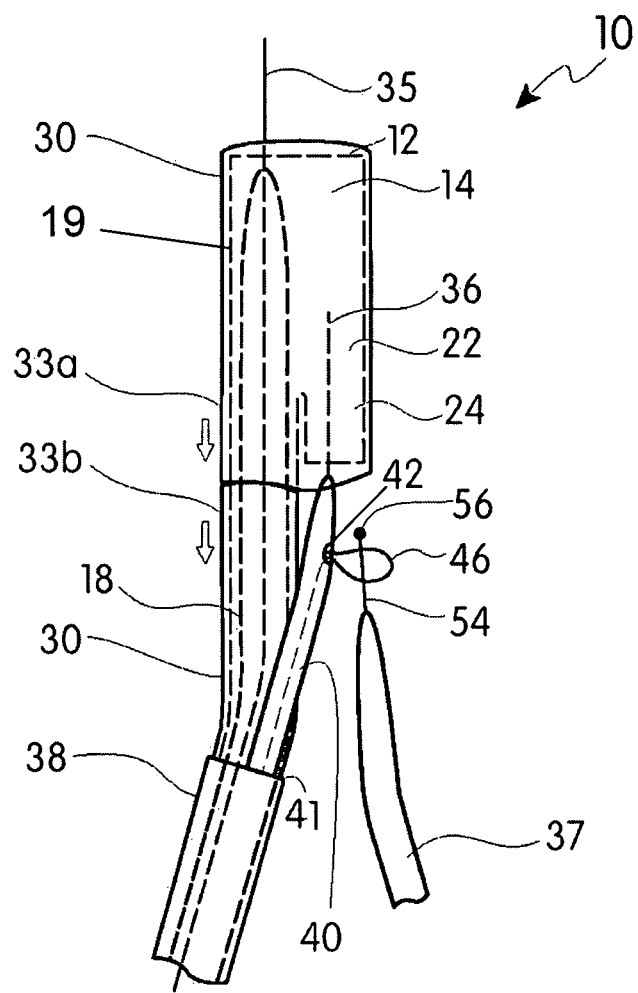
FIG. 1 is a depiction of the device showing a delivery catheter having a snare capture component extending from an exposed aperture in an escort catheter.

Referring now to the drawings in FIGS. 1-10, wherein similar parts are identified by like reference numerals, the device 10 is depicted in FIG. 1 which illustrates the components of the bifurcating prosthesis 12 engaged to the distal end of a delivery catheter 38. A trunk portion 14 is shown having a diameter adapted to engage within the walls of the aorta 16 shown in FIGS. 4-6. The trunk portion 14 is in communication with two smaller conduits extending from a lower end of the trunk 14, communicating with the larger open aperture at the upper end of the trunk 14. An ipsilateral or first leg 18 shown in FIG. 1 and FIGS. 4-10, has a diameter and a length adapted to extend into an engaged position communicating between the trunk 14 and one of the iliac arteries. The other shorter conduit shown in FIGS. 1 and 2a, is a cuff 22 portion extending from the lower end of the trunk 14 portion. As shown in other figures such as FIG. 10, the distal end 24 of the cuff 22 is adapted for engagement to one end of the contralateral or second leg 28 of the assembled device 10 as depicted in FIG. 10.

In use adapted for deployment, the trunk 14, first leg 18, and cuff 22 forming the first component are initially in a collapsed position and held in that state by means of a releasable restraint adapted to the task, which is shown in FIG. 1 as a fabric sheath 30 having a release stitch 31 as a release mechanism to deploy the restraint as best shown in FIG. 2a. The release stitch 31 shown in FIG. 2a, is a chain-type stitch and incrementally releasable by traction on the release string 32 slidably engaged through the first delivery catheter 38 to allow release of the sheath 30 or other releasable restraint, in two segments 33a and 33b, for a staged deployment of the device 10 from its collapsed position in FIG. 2a.

As depicted in FIGS. 1 and 2a, in a preferred mode of the device 10, the restraint would provide for two separately releasable component sections 33a and 33b in a sequential releasable restraint of the bifurcated prostheses 12 which allows for sequential expansion of the first component 19 (comprising the trunk 14 and cuff 22), and subsequently the ipsilateral leg 18 in sequential steps and at appropriate times chosen by the surgeon. The second leg 28 shown in the FIG. 10, is engaged to a second delivery catheter 34 in a collapsed state for translatable delivery along a positioned guide wire 55 to an engagement with the expanded cuff 22. The leading end 29 of the contralateral or second leg 28 shown in FIG. 10, is adapted to cooperatively engage with the distal end 24 of the expanded cuff 22.

The first delivery catheter 38 is advanced through an axial passage running through the interior of the first leg 18 over a first guide wire 35. As shown in FIGS. 1 and 2a, the escort catheter 40 is slidably engaged with the first delivery catheter 38 and with its distal end projecting from an exit aperture 41 in the first delivery catheter 38 as depicted in FIGS. 1 and 2a. In this configuration the distal end of the escort catheter 40 is covered in an engagement under the first release component 33a to maintain the escort catheter 40 streamlined and adjacent to the delivery catheter 38 during initial deployment (FIG. 2a).

A second guide wire 36 projects from the distal end of the escort catheter 40 and is pre-positioned within the cuff 22 prior to compression of the first component 19 to the collapsed state in which it is held by the releasable component sections 33a and 33b depicted in FIG. 1, or other means of sequentially releasable restraint. As shown in FIG. 2a this distal end engagement may be accomplished by passage of the tip of the escort catheter 40 through the release stitch 31 thereby allowing for easy sequential release by the surgeon of the first component section 33a along with the escort catheter 40. The second guide wire 36 thus remains pre-positioned in the cuff 22 for subsequent employment as a guide into the cuff 22 once the first releasable component 33a is released expanding the trunk 14 and cuff 22.

Figure 2:
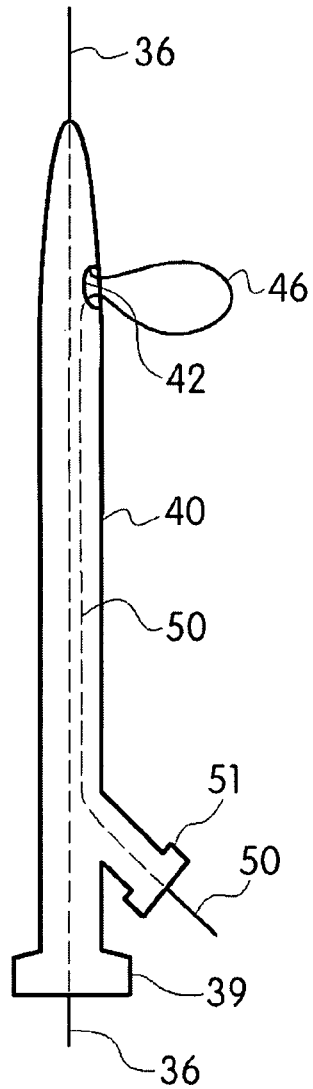
FIG. 2 depicts the escort catheter and an extending snare and control wires.
Figure 2A:
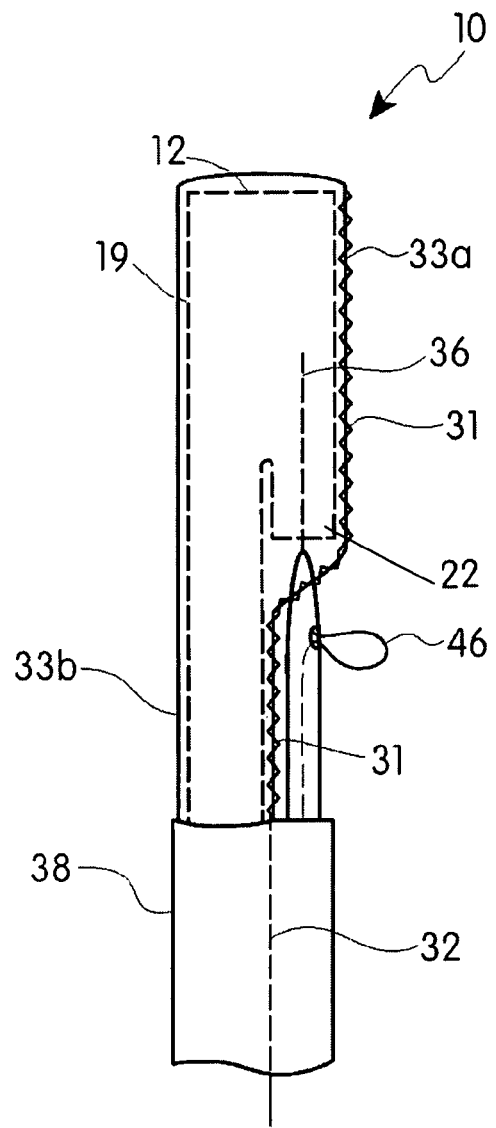
FIG. 2a depicts the device incorporated into the delivery catheter and a release stitch providing a two-stage release of a restraint during deployment.
Figure 3:
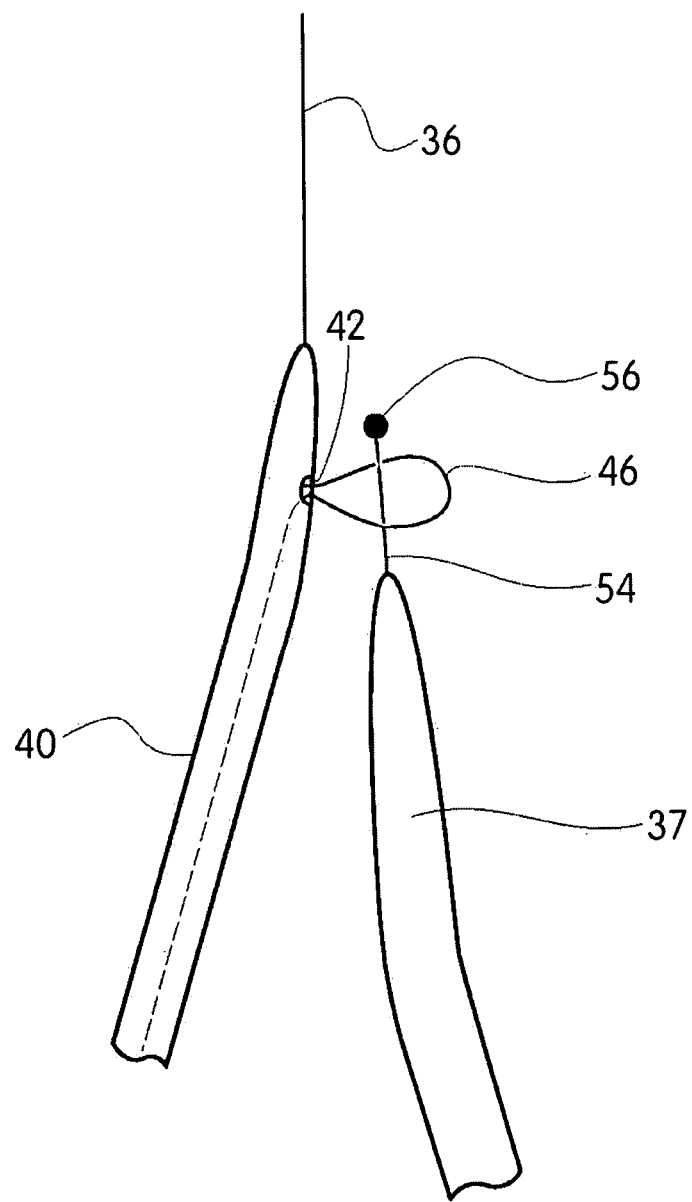
FIG. 3 depicts the capture of a third guide wire using a snare extendable from the escort catheter.

In a preferred mode of the device 10 shown in various views in FIGS. 1-3, communicating from an exit aperture 42 in the escort catheter 40, is a wire capturing means shown as a snare 46 in FIG. 2a. The snare 46 is preferably formed of memory material such as nitinol to a predetermined preferred deployed shape and controllable size by the operator. A snare control wire 50, or other means for cinching and expanding the projecting snare 46, is tranlatably engaged axially through the escort catheter 40 and through a locking valve 51 positioned exterior to the body of the patient. The snare 46 can thus be extended to a loop of a desired size or collapsed by translation of the control wire 50 and held in that position by the locking valve 51.

Figure 8:
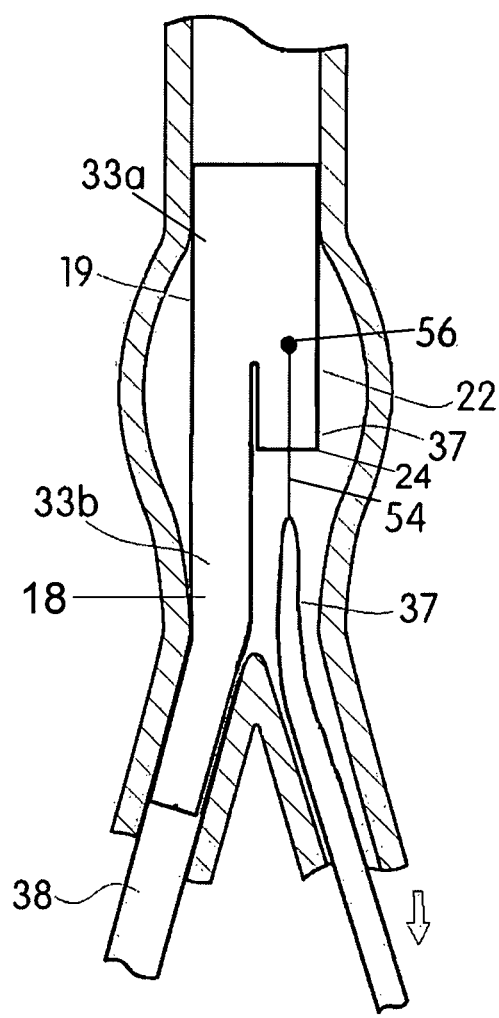
FIG. 8 shows the third guide wire positioned in the cuff after release of the snare and removal of the escort catheter.

During implantation, the first component 19 shown expanded in FIG. 8, formed of the trunk 14, first leg 18, and cuff 22, and shown in FIG. 1 in a collapsed position on the distal end of the first delivery catheter 38, is translated over the pre-positioned first guide wire 35 (FIG. 1), through a femoral artery. The first component 19 in the collapsed position is advanced to a position within the aorta so that the aperture 42 of the escort catheter is adjacent to the juncture of the second iliac artery and the aorta.

Prior to the sequential release of the compressed first component 19, and once the surgeon has determined proper placement in the aorta, the snare 46 is deployed from the exit aperture 42 in the escort catheter 40, to form a loop by employment of the snare control wire 50. The loop of the snare 46 as noted, is properly positioned by the surgeon at the juncture of the second iliac artery and the aorta. Means for positioning of the snare 46 is provided by one or a combination of extension of the snare 46, translation of the delivery catheter 38 and rotation of the delivery catheter 38, to thereby properly deploy the snare 46 extending from the escort catheter 40 in a position for a capture of a third guide wire 54 inserted from the contralateral femoral artery as depicted in FIG. 4.

Figure 4:
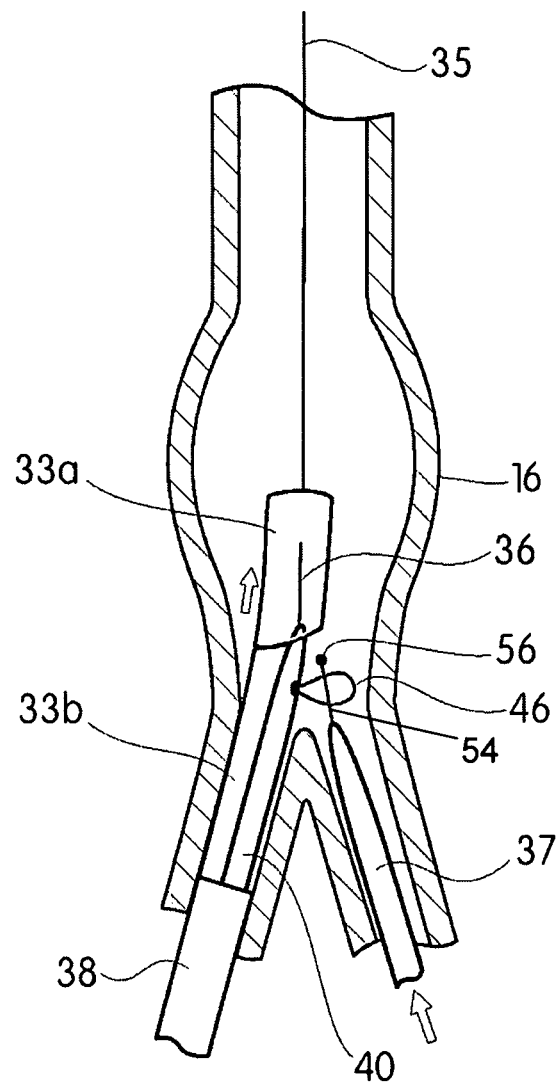
FIG. 4 shows insertion of the delivery catheter to a position at the juncture of the second iliac artery and the aorta and deployment of the snare capture device from the escort catheter.

Upon proper positioning of the first component 19, and the snare 46, a guide catheter 37, having the third guide wire 54 extending from its distal end, is translated through the opposite leg artery shown in FIG. 4. As noted, in a preferred mode of the device 10, the third guide wire 54 is extendable from the distal end of the guide catheter 37 and has a bead 56 or similar means for maintaining a secure capture within the cinched snare 46. Other means to maintain the snare 46 on the third guide wire 54 may be employed as would occur to those skilled in the art and such are anticipated. The main object being that the snare 46 maintains its engagement to the third guide wire 54 during manipulation of the device 10 after the capture, to a desired positioning within the aneurysm. This secured engagement of the cinched snare 46 and escort catheter with the captured third guide wire 54, allows for subsequent translation of the escort catheter 40 along the second guide wire 36, and concurrent translation of the captured third guide wire 54 into the cuff 22 without risk of a detachment therefrom.

As shown in FIG. 4, in the positioning step, the distal end of the third guide wire 54 and the guide catheter 37 are translated to a point wherein the bead 56 passes through the pre-positioned and extended snare 46. Once so positioned, the snare control wire 50 is translated to close the loop and capture the distal end of the third guide wire 54. This cinched snare 46 around the third guide wire 54 behind the bead 56 thereby provides means for positive mechanical engagement of the escort catheter 40 to the third guide wire 54. A locking valve 51 is then set to maintain the snare 46 cinched. As noted, once so captured, the delivery catheter 38 may be manipulated by the surgeon for proper position for deployment of the first component 19 in the aneurysm, as depicted in FIGS. 5-6. During this positioning, capture of the third guide wire 54 is maintained, whether the delivery catheter 38 is translated or rotated.

Figure 7:
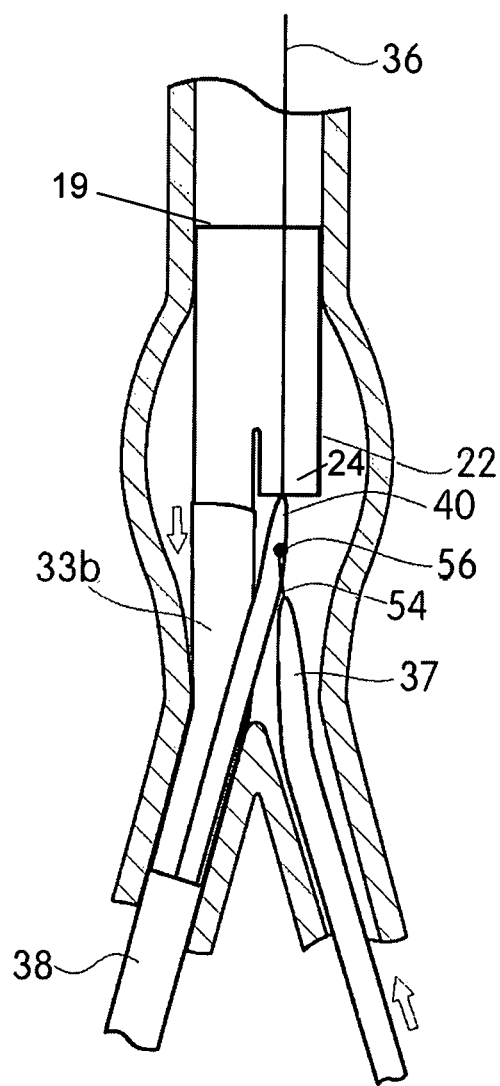
FIG. 7 depicts translation of the escort catheter and captured third guide wire into the expanded cuff.
Figure 7A:
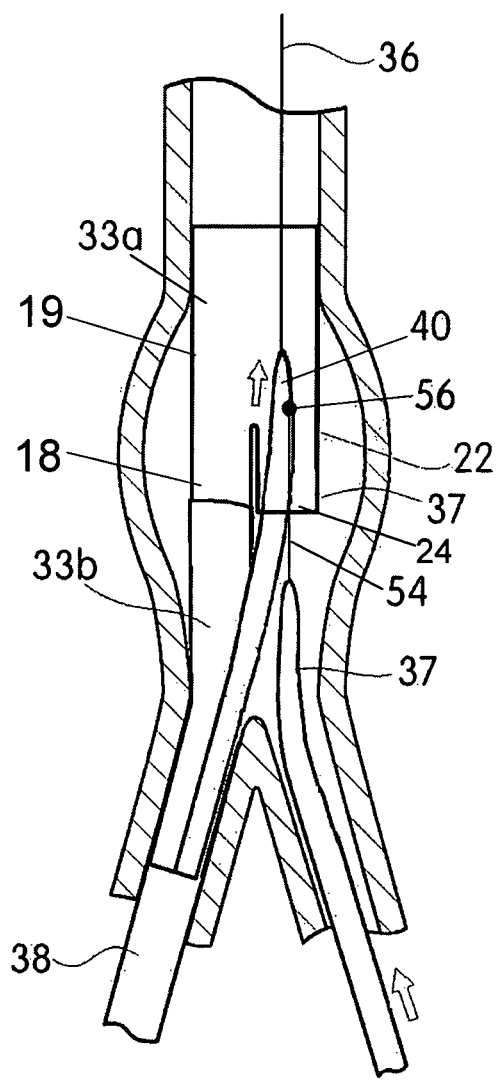
FIG. 7a shows the escort catheter and third guide wire fully translated into the expanded cuff ready for release from its engagement with the snare.

Once the first component 19 is properly positioned, the first releasable portion 33a of the restraining device shown as the sheath 30, is released as shown in FIGS. 6-7. Release as noted is in two stages through the disengagement of the release stitch 31 by translation of the release string 32 (FIG. 2a). Release of the first releasable portion 33a expands the trunk 14 and the cuff 22 in the aorta, and also releases the distal end of the escort catheter 40 from its engagement under the first releasable portion 33a of the fabric sheath 30. The first leg 18 portion in the preferred mode of the device, remains compressed within the second releasable component 33b, for subsequent deployment.

With the third guide wire 54 captured against the side of the escort catheter 40, the escort catheter 40 is now translated along the pre-positioned second guide wire 36 extending into the now expanded cuff 22 as depicted in FIG. 7. This translation of the escort catheter 40 moves the snare-engaged third guide wire 54 into the interior of the cuff 22 easily, thereby eliminating a time-consuming, costly, radiation-intensive and frustrating component in current versions of the procedure.

Once the surgeon ensures passage of the third guide wire 54 into the cuff 22, the snare 46 may be released and the second guide wire 36 and the escort catheter 40 removed. The third guide wire 54 is maintained in position inside the cuff 22 while the escort catheter 40 and snare 46 are removed. With the third guide wire 54 in position, the second releasable portion 33b may be released to deploy the ipsilateral or first leg 18 of the graft in place in the artery. Release of the second releasable portion 33b is accomplished by finishing the unwinding of the release stitch 31 through a translation of the release string 32. Thereafter the first delivery catheter 38 is removed leaving the first component 19 engaged in place in the aorta as shown in FIG. 8.

With the first component 19 so engaged, as will be evident to those skilled in the art, employing the properly positioned third guide wire 54 as a guide, any of a number of conventional wire exchanges may be executed by the surgeon using the third guide wire 54 to properly position subsequent sheaths or guide wires having their distal ends easily positioned inside the cuff 22. For instance the surgeon may advance a wide lumen sheath over the third guide wire 54 to a position with its distal end inside the cuff 22, whereafter the third guide wire 54 may be removed through the wide lumen axial cavity of the sheath. Thereafter a wire 55, of the surgeon's choice, as shown in FIG. 9, may be properly positioned through the axial cavity to place its distal end inside the cuff 22.

Using the wire exchange and the subsequently placed wire 55, the surgeon then advances a secondary delivery catheter 34 thereover to properly position the second component of the bifurcated stent graft 12, which is the contralateral or second leg 28. Such a proper positioning with the leading end 29 the collapsed second leg 28 within the distal end 24 of the cuff 22 is easily accomplished translating the second delivery catheter 34 over the wire 55. So positioned, the second leg 28 is then deployed by activating a secondary release string 58 to release the means for constraint of the second leg 28 from its collapsed position as depicted in FIG. 9 to an engagement with the cuff 22 as depicted in FIG. 10.

The method and components shown in the drawings and described in detail herein disclose arrangements of elements of particular construction and configuration for illustrating preferred embodiments of structure and steps for deployment of the present invention. It is to be understood, however, that elements of different construction and configuration, and using different steps and process procedures, and other arrangements thereof, other than those illustrated and described herein, may be employed for providing for the capture of a second guide wire prior to expansion of a bifurcated endovascular prosthesis in accordance with the spirit of this invention. Further, existing prostheses can be easily adapted to employ the method of assembly and deployment herein described, to deploy a capture device from a catheter which also has a pre-positioned guide wire inside the cuff to later guide that catheter and a captured second guide wire therein. Or, to employ the second catheter and prepositioned wire, to guide any component which can engage with the second catheter, into the cuff portion to be used as a later guide for the leg extension.

As such, while the present invention has been described herein with reference to particular embodiments thereof, a latitude of modifications, various changes and substitutions are intended in the foregoing disclosures, it will be appreciated that in some instance some features of the invention could be employed without a corresponding use of other features without departing from the scope of the invention as set forth in the following claims. All such changes, alternations and modifications as would occur to those skilled in the art are considered to be within the scope of this invention as broadly defined in the appended claims.

Further, the purpose of the abstract of the invention, is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting, as to the scope of the invention in any way.

What is claimed is:

1. A bifurcated stent graft comprising:
a first component having a first end and second end and a central portion therebetween, said first component having a first aperture at said first end, and having an axial passage communicating therethrough;
said first component having a first leg extending from said second end, said first leg having an axial cavity therethrough in communication with said axial passage;
said first component having a second leg extending from said second end, said second leg extending to a distal end and having an axial passageway therethrough in communication with said axial passage;
said first component having a compressed state and an expanded state;
means for restraint of said first component in said compressed state;
means for engagement of said first component at a distal end of a first catheter, said first catheter adapted for translation within an artery to an intersection with a secondary artery;
a second catheter, said second catheter having a distal end translatably positionable relative to said distal end of said first catheter;
a snare, said snare deployable from a position adjacent to said distal end of second catheter;
said snare being retractable to provide a means to removably connect a third guide wire translated through said secondary artery to said second catheter, into a captured state;
a second guide wire axially communicating through said second catheter and extending into said axial passageway of said first component in said compressed state;
a translation of said second catheter upon said second guide wire in a direction toward said first end of said first component, providing means to draw said third guidewire in said captured state, into a deployed position within said axial passageway; and
said third guidewire in said deployed position exchangeable with a secondary guide component, said secondary guide component providing a means to guide an extension of said second leg through said secondary artery and into an engagement with said distal end of said second leg.

2. The bifurcated stent graft of claim 1 additionally comprising:
said second catheter in a slidable engagement with said first catheter.

3. The bifurcated stent graft of claim 2 wherein said slidable engagement of said second catheter with said first catheter comprises:
an axial pathway extending through said first catheter dimensioned for receiving said second catheter therein; and
said distal end of said second catheter extending a distance from an exit aperture in said first catheter, said exit aperture positioned a distance from said distal end of said first catheter.

4. The bifurcated stent graft of claim 3 additionally comprising:
means to maintain said distal end of said second catheter projecting from said exit aperture substantially parallel and adjacent to said first catheter.

5. The bifurcated stent graft of claim 4 wherein said means to maintain said distal end of said second catheter projecting from said exit aperture substantially parallel and adjacent to said first catheter comprises:
said means for restraint of said first component in said compressed state engaging over a portion of said distal end of said second catheter.

6. The bifurcated stent graft of claim 4 wherein said
means to maintain said distal end of said second catheter projecting from said exit aperture substantially parallel and adjacent to said first catheter is said means for restraint of said first component in said compressed state;
said means for restraint of said first component in said compressed state formed of a sheath having a first restraint portion and a second restraint portion;
said distal end of said second catheter held substantially parallel and adjacent to said first catheter by said first restraint portion; and
means to sequentially release said first restraint portion and subsequently said second restraint portion of said sheath.

7. The bifurcated stent graft of claim 1 wherein said means for restraint of said first component in said compressed state additionally comprises:

a release mechanism to release said means for restraint;

said release mechanism providing a sequential release of portions of said first component from said compressed state;

a first release of said portions being a release of said first end, at least a portion of said central portion and said second leg, from said compressed state; and a second release of said portions being a release of said first leg from said compressed state, whereby said translation of said second catheter upon said second guide wire occurs subsequent to said first release.

8. A method of implanting the bifurcated stent graft of claim 1, comprising the steps of:

positioning a first guide wire within an artery;

translating said first component over said first guide wire to a first position in said artery with said second catheter positioned to place said snare adjacent to an intersecting second artery;

translating said third guide wire through said second artery to position adjacent to said snare;

positioning said third guide wire within said snare;

collapsing said snare to capture said third guide wire in a connection to said second catheter;

releasing at least said second leg from said collapsed state;

translating said second catheter along said second guide wire into said axial passageway in a direction toward said first aperture to thereby position said third guide wire connected thereto, within said axial passageway of said second leg;

releasing said snare from said third guide wire and removing said second catheter from said axial passage, employing said third guide wire in an exchange with said secondary guide component and, employing said secondary guide component to guide said leg extension into an engagement with said second leg.

9. The method of claim 8 including the additional steps of:

placing said leg extension into a collapsed state prior to said engagement with said second leg; and releasing said leg extension from said collapsed state; and removing said secondary component previously exchanged for said third guide wire.

10. In a bifurcated stent graft having a collapsed state adapted for translation through a blood vessel and having an expanded state for permanent implantation in said blood vessel and engaged to a first catheter and having a first component having a first end and second end and a central portion therebetween and having a first aperture at said first end, and having an axial passage communicating therethrough with an axial cavity of a first leg and with an axial passageway communicating through a shorter second leg which engages with a separate extension of said second leg which is communicated from a secondary artery, the improvement being:

a second catheter, said second catheter having a distal end translatably positionable relative to said distal end of said first catheter;

a second guide wire axially communicating through said second catheter and having a distal end pre-positioned within said axial passageway of said stent graft while in said collapsed state;

a snare, said snare deployable from a position adjacent to said distal end of second catheter;

said snare being retractable to provide a means to removably connect a third guide wire translated through said secondary artery in captured state in a connection with said second catheter and, whereby subsequent to a release of said stent graft to said expanded state a translation of said second catheter upon said second guide wire, in a direction toward said first end of said first component, provides means to translate said third guide wire connected to said second catheter, into said second axial passageway whereafter said third guidewire is exchangeable with a guide component employable for guiding said extension of said second leg through said secondary artery and into an engagement with said distal end of said second leg.

11. The bifurcated stent graft of claim 10 additionally comprising:

said second catheter in a slidable engagement with said first catheter.

\* \* \* \* \*